United States Patent [19]

Bellamy et al.

[11] 4,058,411

[45] Nov. 15, 1977

[54] DECRYSTALLIZATION OF CELLULOSE

[75] Inventors: Winthrop D. Bellamy; Fred F. Holub, both of Schenectady, N.Y.

[73] Assignee: General Electric Company, Schenectady, N.Y.

[21] Appl. No.: 718,756

[22] Filed: Aug. 30, 1976

[51] Int. Cl.$^2$ .................. C13K 1/02; C08B 15/00
[52] U.S. Cl. .................. 127/37; 127/34; 195/31 R
[58] Field of Search .......................... 127/37

[56] References Cited

U.S. PATENT DOCUMENTS

| 1,906,429 | 5/1933 | Stegemeyer | 127/37 |
|---|---|---|---|
| 3,658,588 | 4/1972 | Harvey | 127/37 X |

OTHER PUBLICATIONS

Chemical Abstracts, 66: 106665y (1967).

Primary Examiner—Sidney Marantz
Attorney, Agent, or Firm—Jane M. Binkowski; Joseph T. Cohen; Jerome C. Squillaro

[57] ABSTRACT

A method for decrystallizing cellulose in natural cellulosic material which comprises admixing phosphoric acid with the cellulosic material to form a gel therewith, admixing tetrahydrofuran with the gel to extract the phosphoric acid forming a solution therewith and a precipitate of amorphous cellulose and recovering tetrahydrofuran and phosphoric acid from the solution for reuse in the process.

3 Claims, 2 Drawing Figures

DECRYSTALLIZATION OF CELLULOSE

The present invention relates to a rapid and convenient process for decrystallizing the cellulose in natural cellulosic material. Specifically, the present process is directed to the conversion of the crystalline regions of cellulose to amorphous form and to the recovery and recycling of the reagents used for such conversion.

Cellulose is a solid natural carbohydrate polymer composed of anhydroglucose units and has the empirical formula $C_6H_{10}O_5$. Cellulose has a physical structure comprised of a mixture of crystalline and amorphous areas or regions. Chemical reagents react with or penetrate the amorphous regions much more readily than the crystalline regions.

Cellulose is the major constituent of vegetable tissues. Wood contains about 50% cellulose whereas cotton fibers contain about 98% cellulose.

Depolymerization of cellulose by acid or enzyme hydrolysis is limited by the degree of crystallization. Both catalysts act more rapidly on the amorphous fractions than the crystalline regions of cellulose. The amorphous and crystalline regions in cellulose fibers behave differently in most chemical reactions such as dyeing, swelling and oxidation. It is, therefore, of interest to determine the crystalline fraction of cellulose. The practical definition used herein is that fraction which is not hydrolyzed by 6N HCl at 100° C for one hour at one atmosphere.

Production of glucose by acid hydrolysis is rate limited because the product of hydrolysis, glucose, is destroyed if the time of contact, temperature and acid concentration are not controlled. Enzyme hydrolysis appears to be rate limited by the number of available sites on the surface of the crystalline regions of cellulose because the large protein molecules cannot penetrate the unswollen crystalline lattice. If an inexpensive, rapid and convenient process for decrystallizing the cellulose in natural fibers were devised it could find wide application. Cellulose could compete with starch as a source of either acid or enzyme produced glucose. It could compete with starch and soluble sugars as a substrate for microbial production of antibiotics and other metabolites, single cell proteins, and industrial alcohol. The many attempts to devise commercial methods for acid hydrolysis of wood and other fibrous plants have not been successful except in times of economic distress such as World War I and II.

Concentrated $H_3PO_4$ has been used as the standard reagent for the preparation of amorphous cellulose from cotton or wood pulp for laboratory and experimental use. After thorough mixing at room temperature and formation of a clear gel, the mixture is washed with large volumes of water until the acid is completely removed. The amorphous cellulose must be kept saturated with water to prevent recrystallization.

The present invention provides a rapid and convenient process for decrystallizing cellulose. In the present invention concentrated $H_3PO_4$ is used to decrystallize cellulose but, in contrast to the prior art, it is extracted and recycled. As used herein the decrystallization of cellulose means the transformation or conversion of all or at least substantially all, i.e. at least about 98% of the crystalline regions of cellulose, to amorphous form.

The present invention will be better understood from the following description taken in connection with the accompanying drawings wherein.

Figure 1:
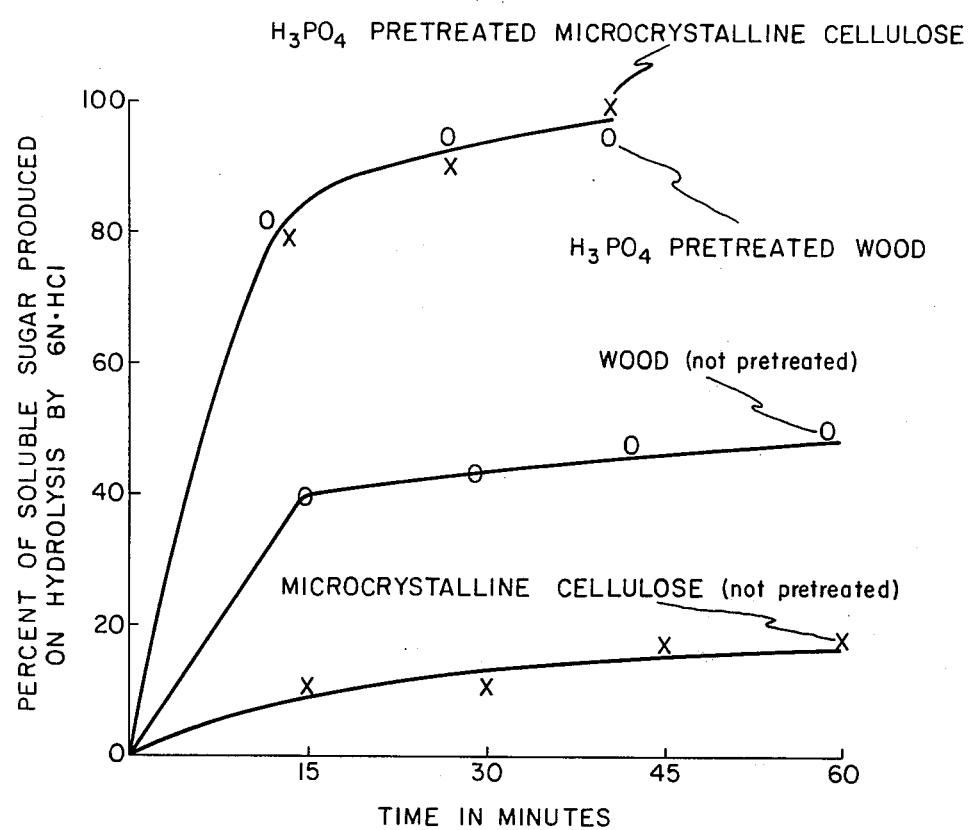
FIG. 1 shows a number of graphs illustrating the effect of $H_3PO_4$ pretreatment on wood and a microcrystalline cellulose sold under the trademark "Avicel" on hydrolysis by 6N HCl.

Briefly stated, the present invention comprises admixing natural cellulosic material with concentrated $H_3PO_4$ acid at room or ambient temperature to form a gel therewith, said $H_3PO_4$ acid transforming the crystalline regions of cellulose to amorphous form, admixing the resulting gel with an aqueous solution of tetrahydrofuran at room or ambient temperature to extract said concentrated $H_3PO_4$ forming a solution therewith and a precipitate of amorphous cellulose, separating said acid-tetrahydrofuran solution, distilling tetrahydrofuran from said acid-tetrahydrofuran solution leaving said phosphoric acid, and admixing water with said precipitate in an amount sufficient to prevent recrystallization of the amorphous cellulose.

The present process utilizes natural cellulosic material. In carrying out the present process the natural cellulosic material is ground in a conventional manner to a suitable mixing size, preferably not larger than about 1 mm. in diameter and length. The ground cellulosic material is then admixed at ambient temperature with concentrated phosphoric acid to produce a thorough mixture. Conventional means can be used to carry out this mixing.

The $H_3PO_4$ ranges in concentration from 80 weight % to 85 weight %. A concentration lower than 80% is not effective whereas a concentration higher than 85% is not useful since at such high concentration the $H_3PO_4$ acid is not fluid. The amount of concentrated $H_3PO_4$ used is determinable empirically and depends largely on the particular cellulosic material and specific concentration of $H_3PO_4$. The concentrated $H_3PO_4$ need only be used in an amount sufficient to form a viscous paste or gel with the ground cellulosic material. Generally, 3 to 10 parts of the concentrated $H_3PO_4$ acid for one part of cellulosic material is useful.

In a preferred embodiment of the present invention, the concentrated $H_3PO_4$ acid is admixed with a surfactant or wetting agent which increases the rate of penetration of the acid into the group cellulosic material thereby increasing the rate of decrystallization of the cellulose and decreasing the amount of mixing required to form a thorough mixture. The surfactant should be soluble and stable in the $H_3PO_4$ acid at ambient temperature, either biodegradable or have no inhibiting effect on microbial growth, and should have no significant deleterious effect on the cellulosic material. The surfactant can be ionic or nonionic. Representative of suitable ionic surfactants are fluorocarbon surfactants with an anionic end group such as a sulphonic acid group and suitable nonionic surfactants are ethoxylated alkylphenols. The amount of surfactant used is determinable empirically and ordinarily ranges from about 0.01 part to 0.5 part of surfactant for 100 parts of the concentrated $H_3PO_4$.

As the concentrated $H_3PO_4$ acid penetrates the ground cellulosic material and forms a gel therewith, it also transforms the crystalline regions of the cellulose to amorphous form. Therefore, once the gel of cellulosic material is formed, it can be treated immediately to extract the phosphoric acid and precipitate the amorphous cellulose.

An aqueous solution of tetrahydrofuran

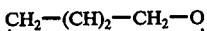

is used to carry out the extraction of phosphoric acid at ambient temperature. Tetrahydrofuran is a liquid which boils at 65° C at one atmosphere. In forming an aqueous solution with the tetrahydrofuran, sufficient water should be used so that the precipitated amorphous cellulose does not recrystallize. The particular amount of water used to form a solution with the tetrahydrofuran is determinable empirically. Ordinarily, about 1 part of water for about 30—100 parts of tetrahydrofuran is useful, and preferably, 1 part of water for every 50 parts of tetrahydrofuran is used.

The amount of aqueous solution of tetrahydrofuran used is determinable empirically and depends on the amount of tetrahydrofuran present in the aqueous solution and the amount of $H_3PO_4$ acid to be extracted. Ordinarily, 1 part to 50 parts of tetrahydrofuran for 1 part of the concentrated $H_3PO_4$ acid is useful.

In the present process not all of the phosphoric acid need be extracted from the gel. A minor portion of the phosphoric acid, about 5% by volume of the cellulose, can be left in the cellulose, if desired, and such phosphoric acid-containing amorphous cellulose is useful as a potential food material for microbial growth.

The extraction is carried out at ambient temperature. In carrying out the extraction, the gel of $H_3PO_4$-containing cellulose material is admixed with the aqueous solution of tetrahydrofuran to form a thorough mixture. Mixing can be carried out by conventional means such as by an extruder or blender. In scale up, for example, a Werner & Pfleiderer twin extruder may be used for mixing the $H_3PO_4$ acid and ground cellulosic material, and a spinerette with multistrandextrusion head used to make continuous or chopped filaments of the resulting gel for dispersion in the aqueous tetrahydrofuran solution. During the mixing tetrahydrofuran extracts the $H_3PO_4$ forming a solution therewith and precipitates amorphous cellulose along with any lignin which may be present. The acid-tetrahydrofuran solution is then separated from the precipitated material by conventional means such as decantation or filtration. The recovered precipitated material is admixed at room temperature with water to form a thorough mixture therewith. The amount of water used in determinable empirically and should be sufficient to saturate the precipitate to prevent recrystallization of the cellulose. Ordinarily, the amount of water ranges from about 1 part to 15 parts per 1 part of precipitate. Preferably, sufficient water is admixed with the precipitate to form a water suspension thereof.

In the present process, while the $H_3PO_4$ acid is transforming the crystalline regions of cellulose to amorphous form, it may act on the amorphous cellulose already present to convert it to glucose, and the resulting gel may be comprised of glucose, amorphous cellulose and $H_3PO_4$. The tetrahydrofuran readily extracts $H_3PO_4$ from glucose-cellulose mixtures without removing a significant amount of the glucose, and a substantial or major amount of glucose present then will precipitate along with the amorphous cellulose.

The solution of tetrahydrofuran and concentrated $H_3PO_4$ is treated to recover the tetrahydrofuran and acid so that each can be used again in the present process. Specifically, to separate the tetrahydrofuran and $H_3PO_4$, the acid-tetrahydrofuran solution need only be heated to the boiling point of tetrahydrofuran to evaporate the tetrahydrofuran and condense it for recycling. Alternatively, tetrahydrofuran can be recovered from the solution by vacuum distillation. The remaining $H_3PO_4$ acid may need to be heated to evaporate water therefrom or add concentrated $H_3PO_4$ or $P_2O_5$ to concentrate it to attain at least about 80% weight concentration.

Figure 2:
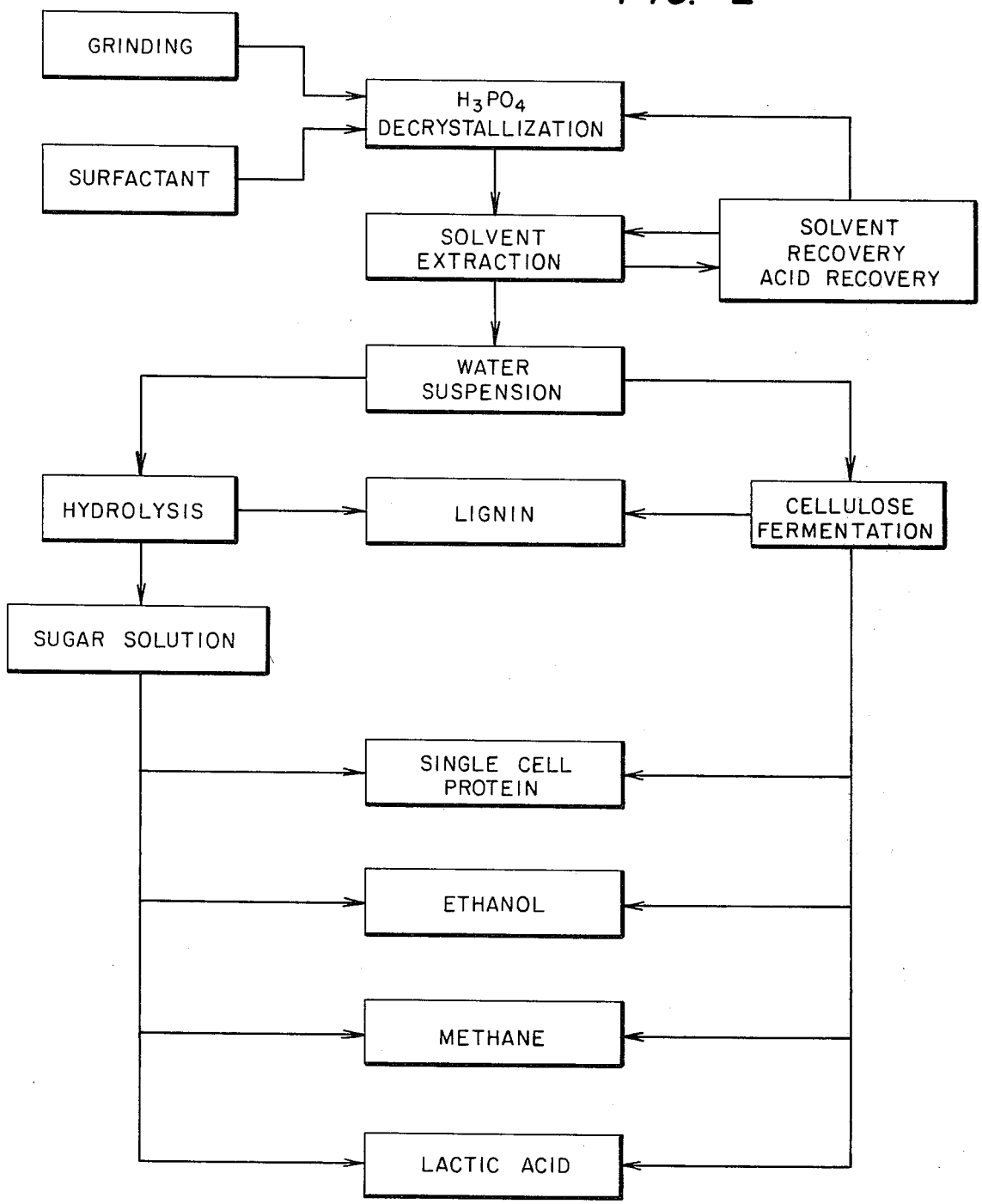
FIG. 2 is a flow diagram illustrating cellulose utilization of the present process.

The water suspension of precipitated amorphous cellulose, and any lignin which may be present, is treated in a conventional manner at room temperature. As shown by FIG. 2, enzymes or acids can be admixed with the suspension to hydrolyze the cellulose to soluble sugars which can be converted to ethanol, lactic acid and other intermediates or to single cell proteins. After hydrolysis or fermentation, any lignin present is filtered away from the aqueous solution to yield the product. Alternatively, the suspension can be admixed with thermophilic or mesophilic, cellulolytic microorganisms to ferment the cellulose directly to single cell proteins, ethanol, lactic acid or methane.

The present process allows the recovery and reuse of phosphoric acid in at least a substantial amount, i.e. from about 85 to about 100% and generally from about 85 to about 95% of the amount originally used to form a gel depending largely on the amount of lignin present since lignin reacts with phosphoric acid to produce a product which is useful as a soil conditioner and fertilizer. Also, the present process allows the recovery and reuse of the tetrahydrofuran in at least a substantial amount, i.e. from about 85% to about 100% and generally from about 85% to about 95% of the amount of tetrahydrofuran initially admixed with the gel.

The invention is further illustrated by the following examples:

EXAMPLE 1

Twenty milligrams of 90 micron size particles of microcrystalline cellulose ("Avicel"), which is completely crystalline, was mixed with two milliliters of 85 weight % $H_3PO_4$ at room temperature. The resulting paste was stirred with a glass rod until a smooth transparent gel was formed. The gel was diluted with ten volumes of a 98 volume % tetrahydrofuran-2 volume % water solution per one volume of gel. On a small bench top scale the best mixing was obtained by extrusion of the gel through 20 gauge needle into a stirred beaker of 20 ml solution of 98 volume % tetrahydrofuran-2 volume % water extracting $H_3PO_4$ from the gel and precipitating amorphous cellulose.

The amorphous cellulose settled as a fine fluffy powder. The precipitate was separated by decantation, washed with a second volume of the aqueous 98% tetrahydrofuran, separated again by decantation and then suspended in water. The total amount of the resulting tetrahydrofuran solution was heated to evaporate tetrahydrofuran therefrom. The remaining aqueous-acid solution was then titrated and found to contain more than 95% the original $H_3PO_4$.

EXAMPLE 2

White pine powder ground to pass a 40 mesh screen was admixed with a sufficient amount of 85 weight % $H_3PO_4$ at room temperature to form a paste which was then stirred with a glass rod until a transparent gel was formed. Because of particles in the gel it could not be extruded, and it was mixed thoroughly with 10 volumes of 98 volume % tetrahydrofuran-2 volume % H₂O per one volume of gel in a mechanical mixer at room temperature. The resulting precipitate was separated by decantation, washed with an additional volume of the aqueous tetrahydrofuran solution, separated again by decantation and then suspended in water at room temperature.

EXAMPLE 3

As indicated in FIG. 1, the cellulose in wood and microcrystalline cellulose ("Avicel"), which had been treated as set forth in Examples 1 and 2, was completely hydrolyzed by 6N HCl at 96° C in less than one hour. Specifically, HCl was added to each water suspension of precipitate produced in Examples 1 and 2 to make 6N HCl and the mixture was then heated at 96° C.

The results of FIG. 1 show that the physical expansion and gel formation observed during mixing with the phosphoric acid was accompanied by a complete decrystallization. Wood contains partially crystalline cellulose as well as hemicelluloses. The latter components are readily hydrolyzed by 6N HCl without pretreatment. However, after $H_3PO_4$ treatment all the available cellulose was hydrolyzed by 6N HCl at 96° C.

EXAMPLE 4

Using $H_3PO_4$ at room temperature substantially as disclosed in Example 1 to decrystallize the microcrystalline cellulose, ("Avicel"), it was determined that at least 82.5 weight % $H_3PO_4$ was necessary for rapid decrystallization at room temperture. Table I presents the yield of amorphous cellulose as determined by settled volume and by 6N HCl hydrolysis.

TABLE I

Decrystallization of microstalline cellulose ("Avicel") as a function of Acid Concentration

| $H_3PO_4$ Wt. % | Settle Volume* | Wt. % Soluble Sugar** |
|---|---|---|
| 0 | 1 mm | — |
| 75 | 8 mm | 32 |
| 77.5 | 20 mm | 40 |
| 80.0 | 63 mm | 76 |
| 82.5 | 61 mm | 94 |
| 85.0 | 59 mm | 100 |

*Settled height of suspension in water after removal of the $H_3PO_4$ and THF.
**After hydrolysis with 6N HCl at 96° for 60 minutes.

EXAMPLE 5

Table II shows that the present $H_3PO_4$ pretreatment has greatly increased the availability of the carbohydrates in wood for the growth of a thermophilic cellulolytic thermoactinomyces microorganism.

TABLE II

The growth of a thermoactinomyces organism on $H_3PO_4$ treated white pine powder

| Sample* | Protein Yield mg | |
|---|---|---|
| | Total | Corrected |
| Control | 0.5 | — |
| White Pine Control | 1.2 | 0.7 |
| White Pine ($H_3PO_4$ treated) | 2.7 | 2.2 |

*Mineral medium with added biotin and thiamin 1mg/l grown 3 days at 55° with shaking. The growth in the 0 control is due to media in the inoculum.

EXAMPLE 6

In this example, a nonionic fluorocarbon surfactant was dissolved in 85 weight % $H_3PO_4$ acid at room temperature. The surfactant was used in an amount of 0.1 part per 100 parts of the acid and was stable in the acid. 1.25 milliliters of the resulting surfactant-$H_3PO_4$ solution were admixed with 250 milligrams of 90 micron microcrystalline cellulose ("Avicel") at room temperature. The resulting paste was stirred with a glass rod until a smooth transparent gel was formed. The rate of penetration of the acid solution into the particles of microcrystalline cellulose was substantially greater than that in Example 1 where no surfactant was used and this was indicated by the decrease in the viscosity during stirring and more rigid gel formation.

The gel was mixed with 10 volumes of 98 volume % tetrahydrofuran-2 volume % water solution per volume of gel at room temperature whereby $H_3PO_4$ was removed from the gel and amorphous cellulose was precipitated.

The precipitate was separated from the tetrahydrofuran wash and admixed with water to form a suspension. HCl was added to the suspension to produce 6N HCl which was heated at 96° C for 1 hour producing reducing sugar in an amount of 96% by weight of the precipitate.

EXAMPLE 7

The procedure used in the example was substantially the same as set forth in Example 6 except that white pine powder was used instead of the microcrystalline cellulose.

Specifically, 250 milligrams of the white pine powder, ground to pass a 40 mesh screen, was admixed with 2.5 milliliters of the surfactant-$H_3PO_4$ solution disclosed in Example 6.

The rate of penetration of the acid solution into the white pine powder was substantially greater than that in Example 2 where no surfactant was used and this was indicated by the decrease in viscosity and more rapid gel formation.

The resulting gel was mixed with the aqueous tetrahydrofuran solution and the resulting precipitate was mixed with water and HCl to make as set forth in Example 6 6N HCl. the resulting mixture was heated at 96° C for one hour and produced reducing sugar in an amount of 89% by weight of the precipitate which was an increase of 46%.

The present invention can be of importance in those areas of the world where conventional food crops are difficult to grow, but fibrous plants grow readily. It also finds application in the production of methane, ethylene, and ethanol from cellulose. This method permits continuous or batch polymer processing for both food production and other applications of amorphous cellulose. The present process causes no loss or no significant loss of the cellulose in the natural cellulosic material.

What is claimed is:

1. A process for decrystallizing cellulose in natural cellulosic material which comprises grinding said natural cellulosic material to a size of about 1 millimeter or less in diameter and length, admixing at ambient temperature phosphoric acid with the ground natural cellulosic material to form a gel-like mixture, said phosphoric acid ranging in concentration from 80 weight % to 85 weight % and being used in an amount sufficient to form said gel-like mixture, said phosphoric acid ranging in amount from 3 to 10 parts for one part of said cellulosic material transforming the crystalline regions of said cellulose to amorphous form, admixing at ambient temperature an aqueous solution of tetrahydrofuran with said gel-like mixture to extract said phosphoric acid therefrom forming a solution therewith and a precipitate of amorphous cellulose, said aqueous solution of tetrahydrofuran being comprised of 1 part of water for about 30 to 100 parts of tetrahydrofuran, said tetrahydrofuran being used in an amount sufficient to extract the phosphoric acid in at least a substantial amount, separating the resulting phosphoric acid-tetrahydrofuran solution from said precipitate, admixing the resulting separated precipitate with water at ambient temperature to form a water suspension thereof, and separating and recovering at least a substantial amount of said tetrahydrofuran and said phosphoric acid from the resulting phosphoric acid-tetrahydrofuran solution by distilling said tetrahydrofuran from said phosphoric acid-tetrahydrofuran solution.

2. A process according to claim 1 wherein said aqueous solution of tetrahydrofuran contains at least 1 part of tetrahydrofuran for each part of phosphoric acid to be extracted.

3. A process according to claim 1 wherein about 0.01 part to 0.5 part of surfactant is admixed with 100 parts of said concentrated $H_3PO_4$ acid, said surfactant being soluble and stable in said concentrated $H_3PO_4$ acid at room temperature and having no significant deleterious effect on said cellulosic material.

* * * * *